United States Patent [19]

Walsh

[11] Patent Number: 5,095,895

[45] Date of Patent: Mar. 17, 1992

[54] NEGATIVE PRESSURE ERECTION APPARATUS

[75] Inventor: Michael W. Walsh, St. Paul, Minn.

[73] Assignee: Dacomed Corporation, Minneapolis, Minn.

[21] Appl. No.: 522,200

[22] Filed: May 11, 1990

[51] Int. Cl.⁵ .............................................. A61F 5/00
[52] U.S. Cl. ..................................................... 600/39
[58] Field of Search ......................................... 128/79

[56] References Cited

U.S. PATENT DOCUMENTS

| D. 258,690 | 3/1981 | Wu | 128/79 |
|---|---|---|---|
| 1,117,618 | 11/1914 | Ach | 128/79 |
| 1,225,341 | 5/1917 | Lederer | 128/79 |
| 2,874,698 | 2/1958 | Sell | 128/79 |
| 3,631,853 | 1/1972 | Burdette, Jr. | 128/79 |
| 3,744,486 | 7/1973 | Wilson | 128/79 |
| 4,378,008 | 3/1983 | Osbon, Sr. | 128/79 |
| 4,539,980 | 9/1985 | Chaney | 128/79 |
| 4,628,915 | 12/1986 | Chaney | 128/79 |
| 4,718,411 | 1/1988 | Stewart | 128/79 |

FOREIGN PATENT DOCUMENTS

| 0148586 | 7/1985 | European Pat. Off. | 128/79 |
|---|---|---|---|
| 8706822 | 11/1987 | PCT Int'l Appl. | 128/79 |

OTHER PUBLICATIONS

Brochure entitled "Safe, Effective, Clinically Tested . . . Treatment for Male Sexual Dysfunction" by Mission Pharmacal Company, San Antonio, Tex. 78296.

Primary Examiner—Cary E. O'Connor
Attorney, Agent, or Firm—Merchant, Gould, Smith, Edell, Welter & Schmidt

[57] ABSTRACT

An apparatus for assisting in erection of a penis, comprising:
an elongated vacuum cylinder sized for accommodating the penis in an erect state, the cylinder being open at a first end to receive the penis in an interior of the cylinder; and
a vacuum pump mounted at the second end of the cylinder and in fluid communication with the interior of the cylinder, the pump including a handle portion reciprocally movable along an axis parallel to a longitudinal axis of the cylinder, the pump evacuating the cylinder upon reciprocal movement of the pump handle so as to create a partial vacuum.

9 Claims, 2 Drawing Sheets

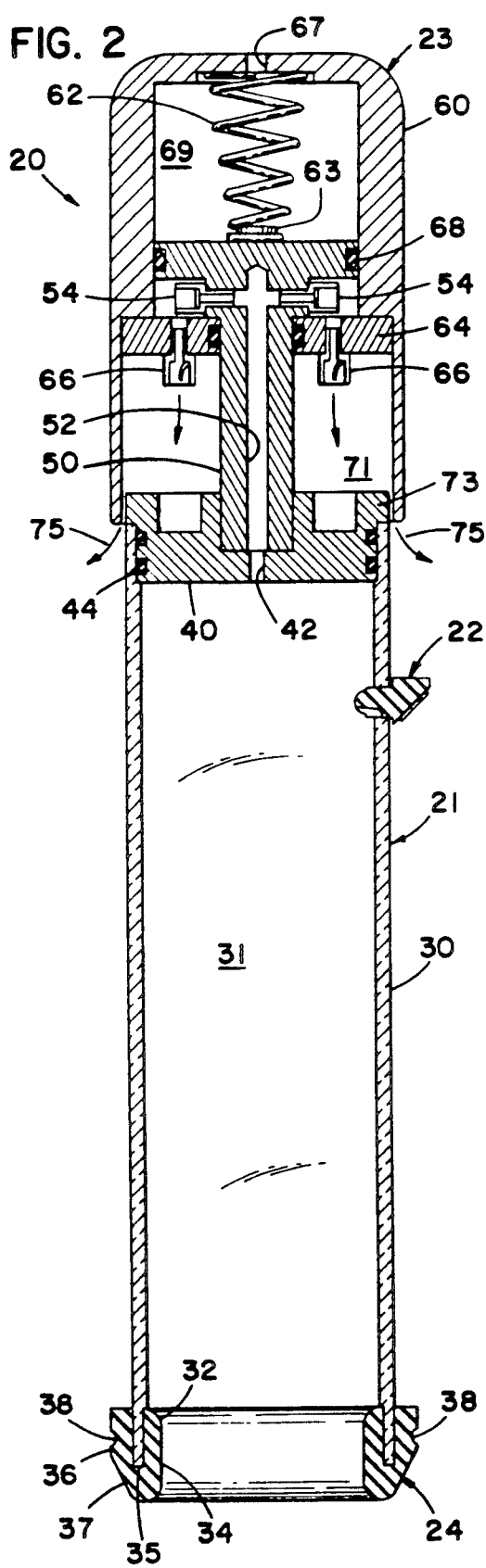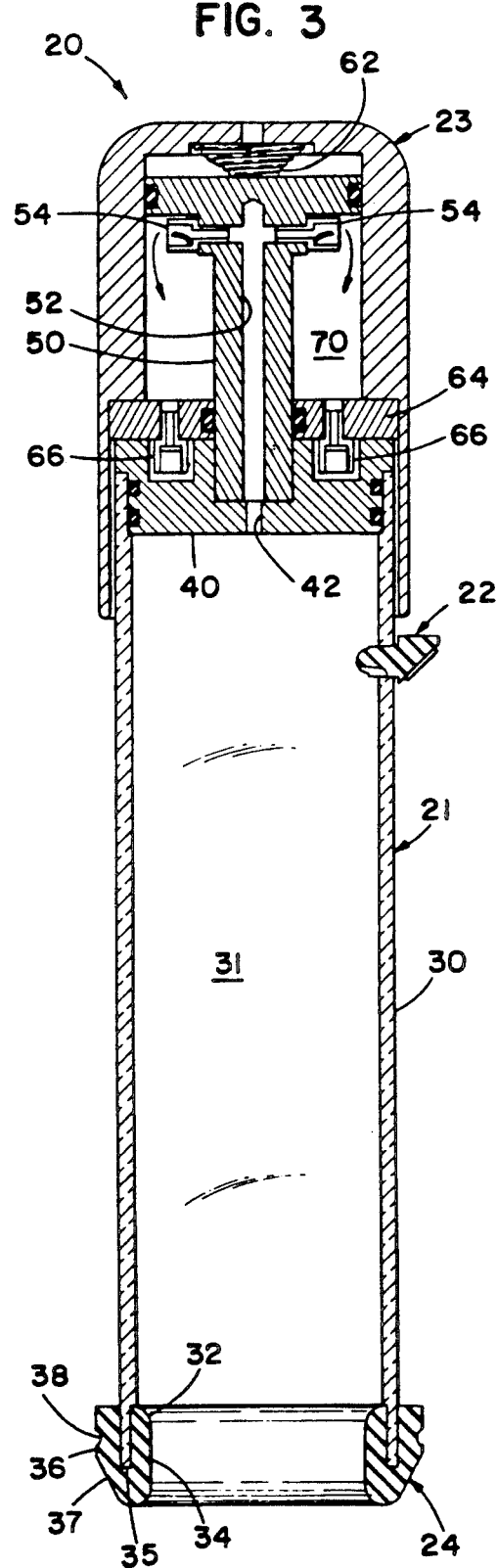

NEGATIVE PRESSURE ERECTION APPARATUS

BACKGROUND OF THE INVENTION

The present invention relates to an apparatus for producing a penile erection.

The inability of one to attain and/or maintain a penile erection is referred to as impotency. There are numerous causes of impotency. Some of these causes are psychological causes and some of these causes are physiological. The applicant has developed various impotency testing devices for use in diagnosing the cause of impotency. For example, see U.S. Pat. Nos. 4,474,187, 4,515,166, 4,766,909, 4,606,353, and 4,848,361.

Once impotency is diagnosed, there is a need for devices which will aid one in attaining and maintaining an erection. There are various surgically implantable devices which enable one to simulate a natural penile erection. The applicant has developed several such devices. For example, see U.S. Pat. Nos. 4,517,967, 4,522,198, 4,541,420 and 4,881,531. While the surgically implantable devices are effective in simulating a natural penile erection, the implantable devices require surgery and typically require a person to spend some time in the hospital.

Devices for producing an erection of the penis have been developed which can be applied externally of the penis without the need for surgery. Many of these devices assist the natural penile erection process by causing blood to flow into the erectile tissue of the penis and then retaining the blood in the erectile tissue.

The operation of these devices can probably be best understood if one understands how a natural erection occurs.

The penis comprises erectile tissue having a sponge-like structure containing cavernous spaces for being occupied by blood. The cavernous spaces are fed by small arteries and capillaries and are drained by small flow restricting veins. Muscles fibers traverse the walls of the spaces and surround the small veins. When the penis is induced to erect, the small arteries dilate, the muscles around the spaces relax, and the muscles surrounding the small veins contract to restrict blood discharge from the spaces of the erectile tissue. The erectile tissue expands as blood is under pressure is pumped into the cavernous spaces, thereby causing the penis to become hard and erect. The natural process of erection is thus basically a matter of causing blood to flow through the arteries under pressure into the erectile tissue and retaining the blood in the erectile tissue by restricting the veins so that the pressurized blood in the erectile tissue cannot flow back through the veins.

Externally applied erection devices are disclosed in U.S. Pat. Nos. 4,539,980, 4,628,915, 4,378,008, 1,225,341, 2,874,698, 1,117,618, 3,744,486, and Des. 258,690. U.S. Pat. No. 4,378,008 discloses an erection device which includes an evacuation chamber. The evacuation chamber includes a sealing flange adjacent which a base is carried flush for carrying an elastic band. A flexible conduit connects the evacuation chamber to a vacuum source. A valve is disposed along the flexible conduit for holding a partial vacuum in the evacuation chamber.

In use, the penis is inserted into the evacuation chamber with the sealing flange engaging the pelvic area. The vacuum source is then activated to create a partial vacuum in the evacuation chamber so as to cause blood to flow into the erectile tissue of the penis thereby causing an erection. As the blood is drawn into the erectile tissue, the penis lengthens and expands to a distended configuration. When the desired erection is obtained, the valve is closed to hold the partial vacuum in the evacuation chamber. The elastic band is then removed from the device and placed about the base of the penis so as to retain the blood in the erectile tissue. The valve is then opened to release the vacuum and the evacuation chamber removed. The elastic band about the base of the penis facilitates retention of the erection for a period of time after the evacuation chamber has been removed.

While the above described device is relatively noninvasive, it does have problems associated therewith. The present invention solves these problems and other problems associated with externally applied devices.

SUMMARY OF THE INVENTION

The present invention relates to a penile erection apparatus.

The present invention provides a practical means for achieving tumescence which is easy to understand and use. It provides a non-threatening, less complicated solution to non-invasive treatment of impotence.

One embodiment of the present invention includes an apparatus for assisting in erection of a penis, comprising:

an elongated vacuum cylinder sized for accommodating the penis in an erect state, the cylinder being open at a first end to receive the penis in an interior of the cylinder; and a vacuum pump mounted at the second end of the cylinder and in fluid communication with the interior of the cylinder, the pump including a handle portion reciprocally movable along an axis parallel to a longitudinal axis of the cylinder, the pump evacuating the cylinder upon reciprocal movement of the pump handle so as to create a partial vacuum.

Yet another embodiment of the present invention includes an apparatus for assisting in erection of a penis, comprising:

an elongated vacuum cylinder sized for accommodating the penis in an erect state, the cylinder being open at a first end to receive the penis in an interior of the cylinder;

vacuum source means being in fluid communication with an interior of the cylinder for creating a partial vacuum in the interior of the cylinder; and self sealing, pressure adjust valve means for reducing the partial vacuum in the interior of the cylinder.

Still another embodiment the present invention includes an apparatus for assisting in erection of a penis, comprising:

an elongated vacuum cylinder sized for accommodating the penis in an erect state, the cylinder being open at a first end to receive the penis in an interior of the cylinder;

vacuum source means being in fluid communication with an interior of the cylinder for creating a partial vacuum in the interior of the cylinder; and a deformable, removable sealing flange being mounted at the first end of the cylinder, the removable sealing flange having an elastic band receiving surface.

One advantage of one embodiment of the present invention is that it provides a vacuum pump which has a natural pumping action which is easy to use. Moreover, the vacuum pump can be readily operated with one hand while the erection is held in position.

Another advantage of one embodiment of the present invention is the inclusion of a pressure relief valve which enables adjustment of the amount of partial vacuum or negative pressure in the vacuum cylinder of the device so as to allow the desired penile erection to be achieved. This also provides for increased comfort and ease of use since if too much of a partial vacuum is achieved, it can be readily adjusted to decrease the pressure exerted on the penis.

Still another advantage of one embodiment of the present invention is the inclusion of deformable, removable seal rings on the vacuum cylinder of the erection device. Accordingly, the seal rings can be readily interchanged with seal rings of various configurations and removed for sanitation purposes. The seal rings cooperates with the vacuum cylinder when inserted onto the end of the vacuum cylinder so as to retain their diameter during the erection process.

These and various other advantages and features of novelty which characterize the invention are pointed out with particularity in the claims annexed hereto and forming a part hereof. However, for a better understanding of the invention, its advantages, and the objects obtained by its use, reference should be made to the accompanying drawings and descriptive matter, which form a further part hereof, and in which there is illustrated and described a preferred embodiment of the invention.

BRIEF DESCRIPTION OF THE DRAWINGS

In the drawings wherein corresponding reference numerals generally indicate corresponding parts throughout the several views;

FIG. 2 is an enlarged sectional view of the embodiment shown in FIG. 1 with a pump head of the device shown in a normal position;

FIG. 3 is a sectional view similar to that of FIG. 2 with the pump head of the device being shown in a compressed position;

DETAILED DESCRIPTION OF PREFERRED EMBODIMENT(S)

Figure 1:
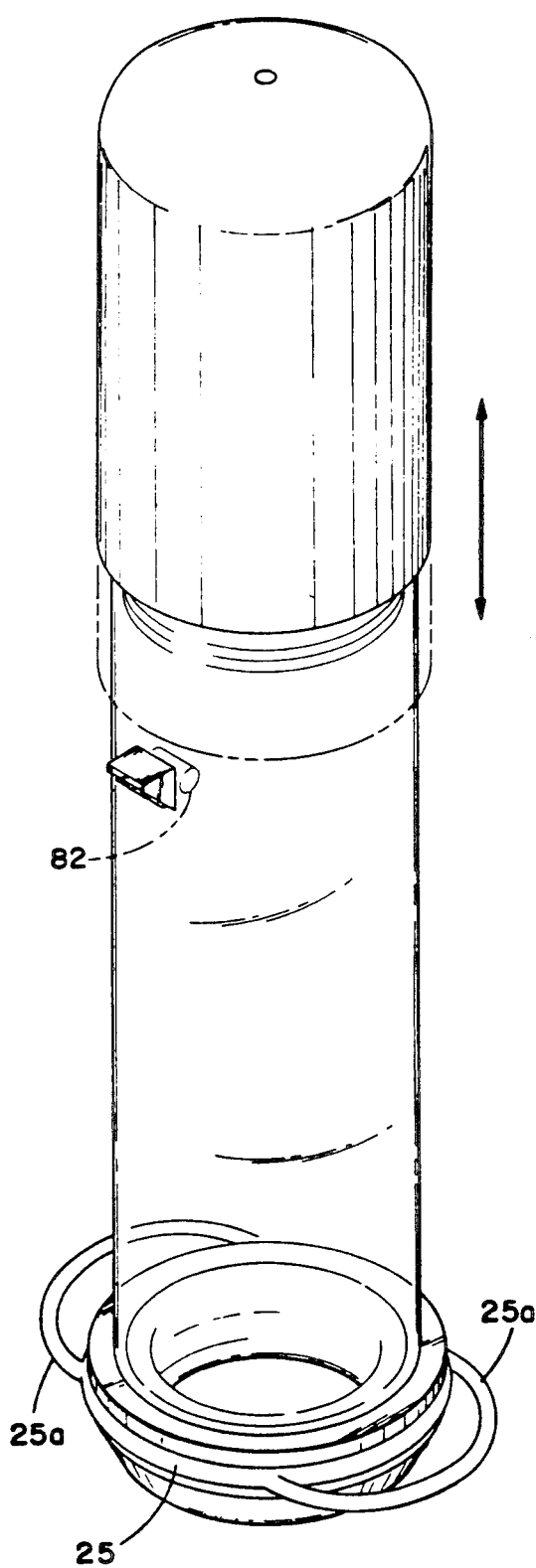
FIG. 1 is a view in perspective of a preferred embodiment of an erection apparatus in accordance with the principles of the present invention.

Referring now to the figures, there is illustrated a preferred embodiment of a non-invasive, externally applied erection apparatus in accordance with the principals of the present invention, the erection apparatus being generally referred to by the reference numeral 20. As is illustrated in the perspective view of FIG. 1, the erection apparatus 20 includes a vacuum cylinder 21, a pressure adjust valve 22 mounted in a wall of the vacuum cylinder 21 for adjustably relieving pressure from a vacuum chamber defined by the vacuum cylinder 21, and a vacuum pump 23 mounted at one end of the vacuum cylinder 21 for a reciprocal movement thereof. Also shown is a deformable, removable sealing flange 24 disposed at an opposite end of the vacuum cylinder 21. The sealing flange 24 is shown removably receiving an elastic ring 25 having handle portions 25a, the elastic ring shown being of a type frequently referred to as a restriction ring.

In use, a male genital organ or penis is inserted into an interior of the vacuum cylinder 21 through the sealing flange end. Prior to this, the penis might be coated with a water soluble lubricant. The vacuum cylinder 21 is held against the pelvis area of the body so as to generally form a seal therewith. The somewhat soft pliable nature of the sealing flange 24 assists in forming a seal. A partial vacuum is then created in the interior of the vacuum cylinder 21 by the user grasping the vacuum pump 23 and reciprocally moving the vacuum pump in a back and forth action. Creation of a partial vacuum in the vacuum cylinder 21 results in the application of an external negative pressure to the penis which results in filling of the penis erection tissues with blood. As the penile tissues are filled with blood, the penis expands in length and girth and becomes rigid. Once the user achieves a satisfactory result, the constriction ring 25 is removed from the sealing flange 24 and placed around the base of the penis to maintain the penile rigidity. Should discomfort result from the creation of the partial vacuum, the user can reduce the partial vacuum and thus the external negative force by merely pressing against the pressure adjust valve 22 which then allows air to enter the partial vacuum of the cylinder thereby reducing the partial vacuum to a level which is comfortable. In the preferred embodiment, the pressure adjust valve 22 is self sealing such that upon release of the pressure adjust valve 22, the pressure adjust valve 22 will return to the sealed position.

The embodiment shown in FIG. 1 will now be described in greater detail. FIGS. 2 and 3 are enlarged cross-sectional drawings illustrating the erection device 20 in its first at rest state, FIG. 2, and in its compressed or evacuating state, FIG. 3. In the preferred embodiment, the vacuum cylinder 21 includes a cylindrical wall 30 which is relatively transparent and in one embodiment is made of polycarbonate so as to be relatively rigid. The vacuum cylinder 21 generally defines an evacuation chamber 31. The sealing flange 24 is removably slid onto an end of the vacuum cylinder 21. In the preferred embodiment shown, an interior surface portion 32 of the wall 30 is recessed so as to provide a seat or shoulder portion for receiving an interior wall 34 of the sealing flange 24. The interior wall and an exterior wall 36 of the sealing flange 24 define a groove 35 for receipt of the wall 30. Upon insertion of the cylinder wall 30 into the groove 35 of the sealing flange 24, the sealing flange 24 is provided with structural rigidity in that it maintains its diameter. Prior to insertion onto the vacuum cylinder 21, the sealing flange 24 shown is readily compressible. In addition, the sealing flange 24 is illustrated as including a groove 38 for removable receipt of the elastic ring 25. The sealing flange 24 further includes a ramped surface 37 which assists in removal of the elastic ring 25 from the groove 38 and onto the base of the penis.

At an opposite end of the vacuum cylinder 21 there is a cover plate 40 which includes an aperture 42 therein and seal rings 44 for providing an air tight seal with an interior surface of the wall 30 of the vacuum cylinder 21. Fixedly mounted on the cover plate 40 is a piston 50 including a fluid passageway 52 in communication with the aperture 42. In addition, the piston 50 is shown as including one-way check valves 54. Concentrically mounted on the piston 50 for reciprocal movement relative thereto is a pump handle 60 which is resiliently biased away from a head portion of the piston 50 by a coil spring 62. The coil spring 62 is mounted at one end on the head portion of the valve stem 50 by a raised shoulder portion 63. Slidably mounted along a stem portion of the piston 50 is a plate member 64 which is fixedly attached to an interior surface of the pump handle 60 and includes one-way check valves 66. Seals 68 form an airtight seal between the head portion of the piston 50 and the inner surface of the pump handle. In addition, the pump handle 60 includes an aperture 67 therein so as to allow fluid to escape from an area 69 defined between the head portion of the piston 50 and the pump handle 60. In the preferred embodiment, the coil spring 62 is tapered such that when the pump handle 60 is in the compressed state as shown in FIG. 3, the coil spring 62 nests within itself.

As the pump handle 60 is moved longitudinally of the vacuum cylinder 21 toward the sealing flange 24, the one-way check valves 54 are opened due to the creation of a vacuum in the area 70 which causes fluid to flow from the evacuation chamber 31 to the area 70. As the pump handle 60 is returned to the at rest state as shown in FIG. 2, the one-way check valves 54 close and the one-way check valves 66 are opened due to the creation of increased pressure in the area 70 which causes fluid to flow from the area 70 to an area 71 and then out to the ambient fluid via a passage 73 between the pump handle 60 and the cover plate 40 as is illustrated by arrows 75. In this fashion, by reciprocal movement of the pump handle 60, a partial vacuum is created in the vacuum cylinder 21.

The pump handle 60 might be made of rigid polyvinyl chloride and have an opaque characteristic so as to not show the internal working parts. As discussed above, the vacuum cylinder 21 is preferably clear. This provides the invention with a non-threatening appearance and allows the user to observe the erection process.

Figure 4:
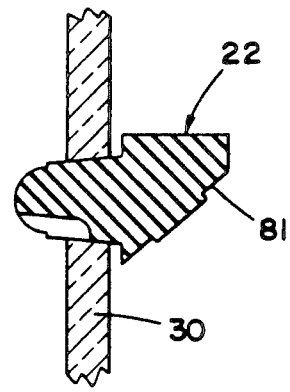
FIG. 4 is an enlarged sectional view a pressure relief/adjustment valve of the embodiment in FIG. 1 being shown in a closed position.
Figure 5:
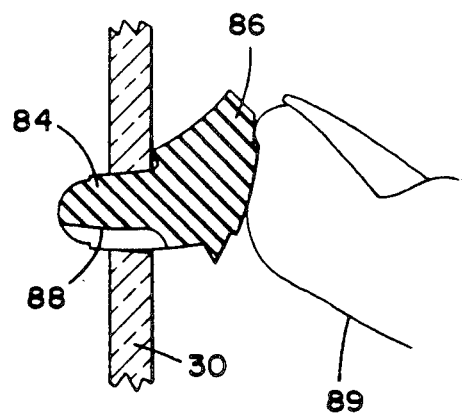
FIG. 5 is a view similar to FIG. 4 with the pressure relief/adjustment valve being shown in an opened position.

Illustrated in FIGS. 4 and 5 are the embodiment of the pressure adjust valve 22. As is illustrated, the pressure adjust valve 22 is made of a very pliable silicon rubber. It includes an inclined surface 81 facing in the direction of the sealing flange 24 and preferably has written indica thereon indicating that it is the pressure adjust valve 22, For example, the word "push" may be printed on this surface. It is this surface which the user presses against to activate the pressure release aspect of the pressure adjust valve 22. The pressure adjust valve 22 is shown as including a cylinder 82 disposed in the interior of the vacuum cylinder 21, a stem portion 84 extending upward through an aperture of the vacuum cylinder 21, and an external portion 86 which includes the surface 81. As is illustrated the stem portion 84 includes a channel 88 part way along the length thereof such that when in the normal at rest position, the pressure adjust valve 22 seals the aperture in the cylinder wall 30. However, when the pressure adjust valve 22 is pressed by use of one's thumb 89 or the like, the channel 88 is exposed to the exterior of the vacuum cylinder 21 so as to provide for fluid communication between the interior of the vacuum cylinder 21 and the exterior thereby enabling fluid, in this case air, to enter the partial vacuum of the vacuum cylinder 21 and relieve the negative pressure being applied. The adjustment valve 22 is readily controllable to allow adjustable relief of the negative pressure.

Figure 6:
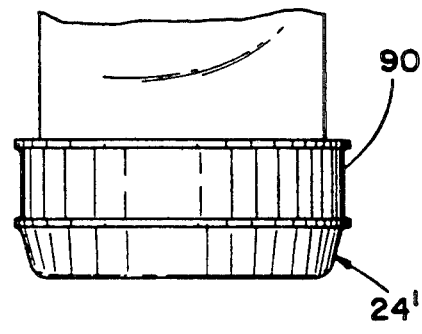
FIG. 6 is a view of an alternate embodiment of a sealing flange.

Referring now to FIG. 6, there is illustrated an alternative embodiment of the sealing flange which is generally referred to by the reference numeral 24'. In this embodiment, the sealing flange 24' includes an enlarged elastic ring receiving surface 90 for receiving either an elastic ring having an enlarged diameter or possibly receiving multiple elastic rings. It will be appreciated that the sealing flange 24 may take on varying configurations in keeping with the principals of the present invention.

It will be appreciated that the large surface area of the piston cylinder 50 will prevent the negative pressure from generally exceeding 15 inches of water in the evacuation chamber 31, thereby adding to the safety of the device since this will prevent the user from creating dangerously high negative pressures.

It is to be understood, that even though numerous characteristics and advantages of the invention have been set forth in the foregoing description, together with details of the structure and function of the invention, the disclosure is illustrative only, and changes may be made in detail, especially in matters of shape, size, and arrangement of the parts within the principles of the invention to the full extent indicated by the broad general meaning of the terms in which the appended claims are expressed.

What is claimed is:

1. An apparatus for assisting in erection of a penis, comprising:
   an elongated vacuum cylinder sized for accommodating the penis in an erect state, the cylinder being open at a first end to receive the penis in an interior of the cylinder; and
   a vacuum pump mounted at and supported by the second end of the cylinder and in fluid communication with the interior of the cylinder, the pump including a stationary piston and a handle portion reciprocally movable along an axis parallel to a longitudinal axis of the cylinder, the pump evacuating the cylinder upon reciprocal movement of the pump handle so as to create a partial vacuum.

2. An apparatus according to claim 1, wherein a deformable sealing flange is removably mounted on the first end.

3. An apparatus according to claim 2, wherein the deformable sealing flange includes an elastic band receiving surface.

4. An apparatus according to claim 2, wherein the deformable sealing flange includes a groove for receiving a wall of the cylinder, the wall cooperating with the deformable sealing flange to increase its rigidity.

5. An apparatus according to claim 1, further including a pressure adjust valve enabling reduction of the partial vacuum in the cylinder.

6. An apparatus according to claim 5, wherein the valve is mounted on a wall of the cylinder, the valve being biased into a normally closed state.

7. An apparatus according to claim 6, wherein the valve includes a resilient one piece member mounted in an aperture in the wall of the cylinder.

8. An apparatus for assisting in erection of a penis, comprising:
   an elongated vacuum cylinder sized for accommodating the penis is in an erect state, the cylinder being open at a first end to receive the penis in an interior of the cylinder; and
   a vacuum pump mounted at the second end of the cylinder and in fluid communication with the interior of the cylinder, the pump including a handle portion concentrically aligned with and telescopically received by the cylinder for reciprocal movement along the axis of the cylinder, the pump evacuating the cylinder upon reciprocal movement of the pump handle toward the first end of the cylinder so as to facilitate sealing the first end of the cylinder and to create a partial vacuum.

9. An apparatus for assisting in erection of a penis, comprising:

an elongated cylindrical housing, the housing comprising first and second cylindrical portions telescopically connected; and a piston disposed within the cylindrical housing, the second cylindrical portion cooperating with the piston to evacuate the interior of the first cylindrical portion upon movement of the second cylindrical portion toward the first end of the first cylindrical portion.

* * * * *